US011305005B2

(12) United States Patent
DiazGranados et al.

(10) Patent No.: US 11,305,005 B2
(45) Date of Patent: Apr. 19, 2022

(54) METHODS OF USE OF INFLUENZA VACCINE FOR PREVENTION OF PNEUMONIA

(71) Applicant: Sanofi Pasteur, Inc., Swiftwater, PA (US)

(72) Inventors: Carlos DiazGranados, Wind Gap, PA (US); Andrew Dunning, Pocono Pines, PA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 110 days.

(21) Appl. No.: 15/738,417

(22) PCT Filed: Jun. 23, 2016

(86) PCT No.: PCT/US2016/038963
§ 371 (c)(1),
(2) Date: Dec. 20, 2017

(87) PCT Pub. No.: WO2016/210093
PCT Pub. Date: Dec. 29, 2016

(65) Prior Publication Data
US 2018/0177861 A1 Jun. 28, 2018

Related U.S. Application Data

(60) Provisional application No. 62/183,888, filed on Jun. 24, 2015.

(51) Int. Cl.
| | |
|---|---|
| *A61K 39/145* | (2006.01) |
| *A61K 39/12* | (2006.01) |
| *A61P 29/00* | (2006.01) |
| *C12N 7/00* | (2006.01) |
| *A61K 39/00* | (2006.01) |

(52) U.S. Cl.
CPC ............ *A61K 39/145* (2013.01); *A61K 39/12* (2013.01); *A61P 29/00* (2018.01); *C12N 7/00* (2013.01); *A61K 2039/545* (2013.01); *A61K 2039/70* (2013.01); *C12N 2760/16034* (2013.01); *C12N 2760/16134* (2013.01); *C12N 2760/16234* (2013.01); *Y02A 50/30* (2018.01)

(58) Field of Classification Search
None
See application file for complete search history.

(56) References Cited

U.S. PATENT DOCUMENTS 9,278,127 B2 * 3/2016 Hanon ................... A61P 37/04
2011/0236376 A1 * 9/2011 Smiley ................ A61K 31/7088
424/133.1

OTHER PUBLICATIONS

Robinson et al., The immunology of influenza virus-associated bacterial pneumonia, 2015, Current Opinion of Immunology, vol. 34, pp. 59-67.*
Martin-Loeches et al., Bacterial pneumonia as an influenza complication, 2017, Current Opinion in Infectious Diseases, vol. 30, pp. 201-207.*
American Lung Association "Relationship between Influenza and Pneumonia." http://www.lung.org/lung-disease/pneumonia/pneumonia-influenza/ pp. 1-2, retrieved from Internet on Jun. 10, 2015.
American Lung Association "Understanding Pneumonia." http://www.lung.org/lung-disease/pneumonia/understanding-pneumonia.htmi pp. 1-3, retrieved from Internet on Jun. 10, 2015.
Anonymous "A Study of Fluzone® High-Dose Vaccine Compared with Fluzone® Vaccine in Elderly Adults." ClinicalTrials.gov, pp. 1-6, retrieved from Internet on Aug. 23, 2016.
Cate et al. "A High Dosage Influenza Vaccine Induced Significantly More Neuraminidase Antibody than Standard Vaccine among Elderly Subjects." *Vaccine*, 28(9): 2076-2079 (2010).
Centers for Disease Control and Prevention "Pneumococcal Vaccination." http://www.cdc.gov/pneumococcal/vaccination.html pp. 1-3, retrieved from Internet on Jun. 10, 2015.
Centers for Disease Control and Prevention "Pneumonia Can Be Prevented—Vaccines Can Help." http://www.cdc.gov/Features/Pneumonia/ pp. 1-5, retrieved from Internet on Jun. 10, 2015.
Chit, et al. "Cost-effectiveness of high-dose versus standard-dose inactivated influenza vaccine in adults aged 65 years and older: an economic evaluation of data from a randomized controlled trial." *The Lancet Infectious Diseases*, 15: 1459-1466 (2015).
Chit, et al. "Expected cost effectiveness of high-dose trivalent influenza vaccine in US seniors." *Vaccine*, 33(5): 734-741 (2015).
Diazgranados, et al. "Efficacy of High-Dose versus Standard-Dose Influenza Vaccine in Older Adults." *New England Journal of Medicine*, 371(7): 635-645 (2014).
Diazgranados, et al. "Prevention of serious events in adults 65 years of age or older: A comparison between high-dose and standard-dose inactivated influenza vaccines." *Vaccine*, 33(38): 4988-4993 (2015).
Dunning, et al. "Correlates of Protection against Influenza in the Elderly: Results form an Influenza Vaccine Efficacy Trial." *Clinical and Vaccine Immunology*, 23(3): 228-235 (2016).
Izurieta, et al. "Comparative effectiveness of high-dose versus standard-dose influenza vaccines in US residents aged 65 years and older from 2012 to 2013 using Medicare data: a retrospective cohort analysis." *The Lancet Infectious Diseases*, 15: 293-300 (2015).
Pavia "What is the Role of Respiratory Viruses in Community Acquired Pneumonia; What is the Best Therapy for Influenza and Other Viral Causes of CAP?" *Infectious Disease Clinics of North America*, 27(1): 157-175 (2013).
Robertson "Fluzone® High-Dose Vaccine and FIM12 Efficacy Trial Results." pp. 1-24 (2014).
Search Report and Written Opinion dated Sep. 7, 2016 in Application No. PCT/US2016/038963, pp. 1-14.

(Continued)

*Primary Examiner* — Benjamin P Blumel
(74) *Attorney, Agent, or Firm* — McNeill Baur PLLC (57) ABSTRACT

This application relates to the field of prevention of pneumonia by administration of a high-dose influenza vaccine.

21 Claims, 9 Drawing Sheets

(56) References Cited

OTHER PUBLICATIONS

Aaberge et al. "Virulence of *Streptococcus pneumoniae* in mice: a standardized method for preparation and frozen storage of the experimental bacterial inoculum" Microb. Pathog. 18: 141-152 (1995).
Brittan et al. Pneumococcal neuraminidase A: an essential upper airway colonization factor for Streptococcus pnenmoniae Mol Oral Microbiol.27(4): 270-283 (2012).
Brown, et al. "The medical dictionary for regulatory activities (MedDRA)" Drug Safety 20(2): 109-117 (1999).
Brundage JF "Interactions between influenza and bacterial respiratory pathogens: implications for pandemic preparedness" Lancet Infect Dis, 6: 303-12 (2006).
Charles et al. "The Etiology of Community-Acquired Pneumonia in Australia: Why Penicillin plus Doxycycline or a Macrolide Is that Most Appropriate Therapy" Clinical Infections Diseases, 46: 1513-1521 (2008).
Falsey et al. "Bacterial Complications of Respiratory Tract Viral Illness: A Comprehensive Evaluation" Journal of Infectious Diseases; 208: 432-441 (2013).
Ferdinands et al. "Inactivated Influenza Vaccines for Prevention of Community-Acquired Pneumonia" Epidemiology; 24: 530-537 (2013).
Gingles NA, et al. "Role of Genetic Resistance in Invasive Pneumococcal Infection: Identification and Study of Susceptibility and Resistance in Inbred Mouse Strains" Infect. Immun; 69: 426-434 (2001).
Gomez-Junyent et al. "Clinical Features, Etiology and Outcomes of Community Acquired Pneumonia in Patients with Chronic Obstructive Pulmonary Disease" Plos One; 8: e105854 (2014).
Gut et al. "Structural basis for Streptococcus pneumoniae NanA inhibition by influenza antivirals zanamivir and oseltamivir carboxylate" Journal of Molecular Biology, 409: 496-503 (2011).
Hayward et al. "Comparative community burden and severity of seasonal and pandemic influenza: results of the Fly Watch cohort study." Lancet Respir Med, 2: 445-54 (2014).
Ishiguro et al. "Etiology and Factors Contributing to the Severity and Mortality of Community-acquired Pneumonia" Internal Medicine; 52: 317-324 (2013).

Lambert and Fauci "Influenza Vaccines for the Future" New England Journal of Medicine; 363: 2036-2044 (2010).
Manco et al. "Pneumococcal Neuraminidases A and B Both Have Essential Roles during Infection of the Respiratory Tract and Sepsis" Infect Immunity; 74(7): 4014-4020 (2006).
Mcelhaney et al. "AS03-adjuvanted versus non-adjuvanted inactivated trivalent influenza vaccine against seasonal influenza in elderly people: a phase 3 randomised trial," The Lancet, pp. 1-11 (2013).
Orihuela et al. "Tissue-Specific Contributions of Pneumococcal Virulence Factors to Pathogenesis," The Journal of Infection Diseases, 190: 1661-1669 (2004).
Said et al. "Estimating the Burden of Pneumococcal Pneumonia among Adults: A Systematic Review and Meta-Analysis of Diagnostic Techniques" Plos One; 8: e60273 (2013).
Trappetti et al. "Sialic Acid: A Preventable Signal for Pneumococcal Biofilm Formation, Colonization, and Invasion of the Host" Journal of Infectious Diseases; 199: 1497-505 (2009).
Verhoeven et al. "Contributions to Protection from Streptococcus pneumoniae Infection Using the Monovalent Recombinant Protein Vaccine Candidates PcpA, PhtD, and PlyD1 in an Infant Murine Model during Challenge" Clinical Vaccine Immunology; 21(8): 1037-1045 (2014).
450/477 Fluzone® Quadrivalent (Influenza Vaccine), 2018-2019 Formula, Highlights of Prescribing Information (Revised Jan. 2019) (8 pages).
FLUVIRIN® (Influenza Virus Vaccine), 2017-2018 Formula, Highlights of Prescribing Information (Revised Mar. 2017) (13 pages).
FluMist® Quadrivalent (Influenza Vaccine Live, Intranasal), Intranasal Spray, 2019-2020 Formula, Highlights of Prescribing Information (Revised Sep. 2019) (6 pages).
Flulaval Quadrivalent (Influenza Vaccine), 2019-2020 Formula, Highlights of Prescribing Information (2019) (27 pages).
Flucelvax Quadrivalent (Influenza Vaccine), 2019-2020 Formula, Highlights of Prescribing Information (Revised Apr. 2019) (6 pages).
Flublok® Quadrivalent (Influenza Vaccine), 2019-2020 Formula, Highlights of Prescribing Information (Revised Jul. 2019) (5 pages).
Fluarix Quadrivalent (Influenza Vaccine), 2019-2020 Formula, Highlights of Prescribing Information (Revised Jul. 2019) (26 pages).
Afluria Quadrivalent, Influenza Vaccine, 2019-2020 Formula, Highlights of Prescribing Information (Revised Mar. 2019) (8 pages).

* cited by examiner

Fig. 1

| | Number of Specified Pneumonias | Efficacy & (95% CI) |
|---|---|---|
| Y1 - Pneumonia within 30 days of lab-confirmed influenza | 1 | Not evaluable |
| Y2 - Pneumonia within 30 days of lab-confirmed influenza | 13 | 55 (-44, 86) |
| Y1+Y2 - Pneumonia within 30 days of lab-confirmed influenza | 14 | 60 (-28, 87) |
| Y1 - Pneumonia within 30 days of RI, regardless of influenza confirmation | 180 | 39 (18, 55) |
| Y2 - Pneumonia within 30 days of RI, regardless of influenza confirmation | 221 | 16 (-10, 35) |
| Y1+Y2 - Pneumonia within 30 days of RI, regardless of influenza confirmation | 401 | 27 (11, 40) |
| Y1 - Serious pneumonia, regardless of influenza confirmation | 83 | 46 (16, 66) |
| Y2 - Serious pneumonia, regardless of influenza confirmation | 106 | 34 (3, 55) |
| Y1+Y2 - Serious pneumonia, regardless of influenza confirmation | 189 | 40 (19, 55) |

Fig. 3

|  | Year 1 | | Year 2 | | Combined (Y1 + Y2) | |
| --- | --- | --- | --- | --- | --- | --- |
|  | IIV-HD<br>N=7253<br>n (%) | IIV-SD<br>N=7244<br>n (%) | IIV-HD<br>N=8737<br>n (%) | IIV-SD<br>N=8749<br>n (%) | IIV-HD<br>N=15990<br>n (%) | IIV-SD<br>N=15993<br>n (%) |
| History of pneumococcal vaccination (at any time before randomization) | 4773 (65.81) | 4732 (65.32) | 5647 (64.63) | 5633 (64.38) | 10420 (65.17) | 10365 (64.81) |
| Pneumococcal vaccination during the study (any time during follow-up) | 268 (3.70) | 254 (3.51) | 303 (3.47) | 310 (3.54) | 571 (3.57) | 564 (3.53) |

Fig. 4

| | IIV-HD (N=15,990) n (rate)* | IIV-SD (N=15,993) n (rate)* | Relative Vaccine Efficacy % (95% CI) |
|---|---|---|---|
| During high influenza incidence [2] | 29 (1.88) | 42 (3.19) | 30.94 (-13.51, 58.51) |
| During moderate influenza incidence [2] | 12 (0.75) | 25 (1.56) | 51.99 (0.84, 78.02) |
| During low influenza incidence [3] | 30 (1.81) | 51 (2.63) | 41.17 (5.85, 63.82) |

\* n = number of serious pneumonia events, rate = events per 1,000 subject-seasons
[1] Defined as from the start of the first week in which the number of laboratory-confirmed influenza cases exceeded 1 per 1,000 subjects until two weeks after the end of the last week in which the number of cases exceeded this rate
[2] Defined as from the start of the first week in which the number of laboratory-confirmed influenza cases exceeded 0.5 per 1,000 subjects until two weeks after the end of the last week in which the number of cases exceeded this rate AND excluding events occurring during [1]
[3] Defined as events not occurring during [1] or [2]

Fig. 5

|  | Year 1 | | Year 2 | | Combined | |
|---|---|---|---|---|---|---|
|  | IIV-HD (N=7253) n (rate)[a] | IIV-SD (N=7244) n (rate)[a] | IIV-HD (N=8737) n (rate)[a] | IIV-SD (N=8749) n (rate)[a] | IIV-HD (N=15990) n (rate)[a] | IIV-SD (N=15993) n (rate)[a] |
| All-cause hospitalization | 797 (109.89) | 793 (109.47) | 733 (83.90) | 850 (97.15) | 1530 (95.68) | 1643 (102.73) |
| Serious cardio-respiratory events | 204 (28.13) | 236 (32.58) | 224 (25.64) | 284 (32.46) | 428 (26.77) | 520 (32.51) |
| Pneumonia events | 29 (4.00) | 54 (7.45) | 42 (4.81) | 64 (7.32) | 71 (4.44) | 118 (7.38) |
| Asthma/COPD/bronchial events | 40 (5.51) | 21 (2.90) | 34 (3.89) | 54 (6.17) | 74 (4.63) | 75 (4.69) |
| Influenza events[b] | 1 (0.14) | 0 (0.00) | 3 (0.34) | 6 (0.69) | 4 (0.25) | 6 (0.38) |
| Coronary artery events | 55 (7.58) | 70 (9.66) | 66 (7.55) | 54 (6.17) | 121 (7.57) | 124 (7.75) |
| Congestive heart failure | 24 (3.31) | 28 (3.87) | 33 (3.78) | 47 (5.37) | 57 (3.56) | 75 (4.69) |
| Cerebrovascular events | 43 (5.93) | 39 (5.38) | 29 (3.32) | 38 (4.34) | 72 (4.50) | 77 (4.81) |
| Other respiratory events | 13 (1.79) | 24 (3.31) | 18 (2.06) | 23 (2.63) | 31 (1.94) | 47 (2.94) |

Abbreviations: IIV-HD: high-dose inactivated influenza vaccine; IIV-SD: standard-dose inactivated influenza vaccine; COPD: chronic obstructive pulmonary disease

[a] n = number of events; rate = events per 1,000 participant-seasons
[b] Corresponding to serious laboratory-confirmed influenza diagnosed outside study procedures by a participant's health-care provider

Fig. 6

| | Year 1 N=14,497 rVE% (95% CI) | Year 2 N=17,486 rVE% (95% CI) | Combined N=31,983 rVE% (95% CI) |
|---|---|---|---|
| All-cause hospitalization | -0.4 (-10.1; 8.5) | 13.6 (5.1; 21.4) | 6.9 (0.5; 12.8) |
| Serious cardio-respiratory events | 13.7 (-3.8; 28.2) | 21.0 (6.1; 33.5) | 17.7 (6.6; 27.4) |
| Pneumonia events | 46.4 (15.9; 65.8) | 34.3 (3.1; 55.4) | 39.8 (19.3; 55.1) |
| Asthma/COPD/bronchial events | -90.2 (-222.3; -12.3) | 37.0 (3.3; 58.9) | 1.3 (-36.0; 28.4) |
| Influenza events[a] | NE | 49.9 (-100.1; 87.5) | 33.3 (-136.2; 81.2) |
| Coronary artery events | 21.5 (-11.5; 44.8) | -22.4 (-75.1; 14.5) | 3.4 (-25.3; 24.0) |
| Congestive heart failure | 14.4 (-47.5; 50.3) | 29.7 (-9.6; 54.9) | 24.0 (-7.2; 46.1) |
| Cerebrovascular events | -10.1 (-69.7; 28.5) | 23.6 (-23.8; 52.8) | 6.5 (-28.9; 32.1) |
| Other respiratory events | 45.9 (-6.2; 72.4) | 21.6 (-45.1; 57.7) | 34.0 (-3.8; 58.1) |

Abbreviations: rVE: relative vaccine effectiveness; CI: confidence interval; COPD: chronic obstructive pulmonary disease; NE: non-evaluable

[a] Corresponding to serious laboratory-confirmed influenza diagnosed outside study procedures by a participant's health-care provider

| Microorganism | Total N=19 | IIV-HD N=6 | IIV-SD N=13 |
|---|---|---|---|
| Influenza A | 3 | 0 | 3 |
| Streptococcus pneumoniae* | 5 | 1 | 4 |
| Staphylococcus aureus (MSSA or MRSA) | 4 | 1 | 3 |
| Escherichia coli | 2 | 1 | 1 |
| Haemophilus influenzae | 1 | 1 | 0 |
| Klebsiella pneumoniae | 1 | 0 | 1 |
| Enterococcus spp. | 1 | 1 | 0 |
| Candida spp. | 1 | 1 | 0 |
| Unspecified "streptococcal pneumonia" | 1 | 0 | 1 |

Fig. 9

METHODS OF USE OF INFLUENZA VACCINE FOR PREVENTION OF PNEUMONIA

CROSS REFERENCE TO RELATED APPLICATIONS

This application is a national phase entry pursuant to 35 U.S.C. § 371 of International Application No. PCT/US2016/038963, filed Jun. 23, 2016, which claims the benefit of priority of U.S. Provisional Application No. 62/183,888, filed Jun. 24, 2015, all of which are incorporated by reference in their entirety for any purpose.

FIELD

This application relates to compositions and methods for preventing pneumonia.

INTRODUCTION AND SUMMARY

Pneumonia is an infection of one or both of a patient's lungs that can be caused by a number of different pathogens, including viruses, bacteria, and fungi. Symptoms of pneumonia include cough, chest pain, fever, and difficulty breathing. Serious complications of pneumonia can include respiratory failure, sepsis, and lung abscesses. When a patient develops pneumonia outside of a hospital without having had recent contact with a healthcare facility (like a hospital, long-term care facility, or dialysis center), it is termed community-acquired pneumonia (CAP). When a patient develops pneumonia following a stay in a healthcare facility, it is termed healthcare-associated pneumonia. The infectious agents that cause CAP and healthcare-associated pneumonia are often different.

Respiratory viruses are recognized as common causes of CAP, particularly among children and the elderly (see Pavia A T (2013) *Infect Dis Clin North Am* 27(1): 57-175). Additionally, respiratory viruses are an important cause of severe pneumonia and respiratory failure in immunocompromised patients. In patients with CAP, respiratory viruses can be the sole cause of viral pneumonia (i.e., primary viral pneumonia), can be present as a co-infection with a bacteria or another virus (i.e., viral-bacterial pneumonia or viral-viral pneumonia), or can act as predisposing factors to facilitate or worsen bacterial pneumonia.

Influenza virus can cause primary viral pneumonia or predispose a patient to bacterial pneumonia. Influenza is a common cause of pneumonia particularly among young children, the elderly, pregnant women, those with chronic health conditions, and those who live in a nursing home. Radiographic pneumonia can be confirmed in approximately 16%-55% of patients hospitalized for influenza. Patients with influenza who are admitted to the hospital are more likely to die or be admitted to the ICU if they also have pneumonia. The American Lung Association reports that flu and pneumonia was the ninth leading cause of death in the United States in 2010 and the seventh leading cause of death among individuals 65 years of age and older.

Many different types of bacteria can also cause pneumonia. The most common cause of bacterial pneumonia in adults is *Streptococcus pneumoniae* (pneumococcus). Available vaccines have decreased the prevalence of pneumococcal diseases, including pneumonia caused by *Streptococcus pneumoniae* (*CDC: Pneumococcal vaccination*).

The Centers for Disease Control estimates that one million people per year are hospitalized with pneumonia in the US, and approximately 50,000 people die from pneumonia (*CDC: Pneumonia Prevention*). Most hospitalizations and deaths from pneumonia in the US are in adults. Globally, pneumonia causes nearly one million deaths in children under 5 years of age, which is greater than that from any other infectious agent, including HIV infection, malaria, or tuberculosis. While certain vaccinations and preventative practices can decrease its risk, pneumonia remains a significant healthcare concern in the US and globally.

The inventors have discovered that when influenza vaccine is administered at a higher than normal dose, it can prevent pneumonia in addition to preventing influenza. In one embodiment, the influenza vaccine's effect on pneumonia is mediated directly through cross-pathogen immune responses. In another embodiment, the influenza vaccine's effect on pneumonia is mediated indirectly through alterations of the nasopharyngeal microbiome. In another embodiment, the influenza vaccine's effect on pneumonia is mediated through a combination of effects.

In one embodiment, the influenza vaccine exerts an effect on pneumonia protection that is independent from its prevention of influenza infection or its corresponding disease modulation. In other embodiments, the influenza vaccine elicits an immune response that prevents pneumonia caused by non-influenza pathogens, like, for example, *Streptococcus pneumoniae*.

In accordance with the description, methods for preventing pneumonia comprising administering an influenza vaccine or a component or components of an influenza vaccine are encompassed. In some embodiments, use of an influenza vaccine or a component or components of an influenza vaccine for preventing pneumonia is provided. In some embodiments, use of an influenza vaccine or a component or components of an influenza vaccine for the manufacture of a medicament for the prevention of pneumonia is provided. In some embodiments, an influenza vaccine or a component or components of an influenza vaccine for use in the prevention of pneumonia is provided.

In some embodiments, the dose of the influenza vaccine administered to a subject is higher than a standard dose influenza vaccine. In some embodiments, the subject is provided with a greater volume of a standard dose vaccine, thereby providing the subject with a higher dose. In other embodiments, the influenza vaccine is formulated to contain a higher dose. In other embodiments, the influenza vaccine has a higher neuraminidase (NA) content when compared to standard dose vaccines. In other embodiments, the influenza vaccine has a higher haemagglutinin (HA) content when compared to standard dose vaccines. In other embodiments, the influenza vaccine has a higher matrix 1 (M1) content when compared to standard dose vaccines. In other embodiments, the influenza vaccine has a higher matrix 2 (M2) content when compared to standard dose vaccines. In other embodiments, the influenza vaccine has a higher polymerase basic 1 (PB1) content when compared to standard dose vaccines. In other embodiments, the influenza vaccine has a higher polymerase basic 2 (PB2) content when compared to standard dose vaccines. In other embodiments, the influenza vaccine has a higher polymerase acidic (PA) content when compared to standard dose vaccines. In other embodiments, the influenza vaccine has a higher non-structural 1 (NS1) content when compared to standard dose vaccines. In other embodiments, the influenza vaccine has a higher non-structural 2 (NS2) content when compared to standard dose vaccines. In other embodiments, the influenza vaccine has a higher nucleoprotein (NP) content when compared to standard dose vaccines. In other embodiments, the influenza vaccine has a higher amount of any combination of one or more of the influenza virus proteins HA, NA, M1, M2, PB1, PB2, PA, NS1, NS2, and NP when compared to standard dose vaccines.

In some embodiments, the pneumonia is caused by a virus, bacteria, or fungi. In some embodiments, the pneumonia is caused by a virus selected from influenza virus, respiratory syncytial virus (RSV), metapneumovirus, adenovirus, rhinovirus, coronavirus varicella-zoster virus, and parainfluenza virus. In some embodiments, the pneumonia is caused by a bacteria selected from the group consisting of *Streptococcus pneumonia, Staphylococcus aureus, Neisseria meningitides, Mycoplasma pneumonia, Haemophilus influenza, Legionella pneumonia, Legionella* spp., *Chlamydia* spp., including *Chlamydia pneumonia*, and *Chlamydia psittaci, Moraxella* spp., including *Moraxella catarrhalis, Streptococcus pyogenes*, including *Streptococcus pyogenes* (Group A), *Pseudomonas aeruginosa*, gram-negative enteric bacilli, methicillin-susceptible *S. aureus*, methicillin-resistant *S. aureus, Haemophilus parainfluenzae, Haemophilus parahaeolyticus, Pseudomonas alcaligenes, Citrobacter freundii, Staphylococcu haemolyticus, Clostridium perfringens*, anaerobes, including *Fusobacterium* sp., *Prevotella* sp., *Gemella morbillorum, Peptostreptococcus prevotii*, and *Veillonella* sp., *nocardia* sp., coagulase-negative *Staphylococci*, and *Acinetobacter baumannii*. In some embodiments, the pneumonia is caused by a fungus associated with at least one of histoplasmosis, coccidioidomycosis, blastomycosis, pneumocystis pneumonia, sporotrichosis, cryptococcosis, aspergillosis, candidiasis, and scedoporiosis. In some embodiments, the pneumonia is caused by a virus and a bacterium.

In some embodiments, the pneumonia is a community-acquired pneumonia (CAP). In some embodiments, the pneumonia is a healthcare-associated pneumonia.

In some embodiments, the pneumonia is caused by infection with influenza virus. In some embodiments, the pneumonia is not preceded by influenza. In some embodiments, the pneumonia is preceded by, or concurrent with influenza.

In some embodiments, the vaccine is administered to a subject at a dose that is higher than that in a standard-dose influenza vaccine. In some embodiments, the vaccine administered to a subject has a hemaeglutinin (HA) content that is higher than the HA content of a standard-dose influenza vaccine. In some embodiments, the vaccine administered to a subject has a neuraminidiase (NA) content that is higher than the NA content of a standard-dose influenza vaccine. In some embodiments, the vaccine administered to the subject has a content of one or more influenza proteins that is higher than the content in a standard-dose influenza vaccine, wherein said influenza protein(s) is selected from HA, NA, M1, M2, PB1, PB2, PA, NS1, NS2, and NP.

In some embodiments, the influenza vaccine is a trivalent vaccine. In some embodiments, the influenza vaccine is a quadrivalent vaccine.

In some embodiments, the vaccine is produced in avian eggs. In some embodiments, the vaccine is not produced in avian eggs. In some embodiments, the vaccine is made by recombinant DNA techniques. In some embodiments, the vaccine is inactivated or live attenuated.

In some embodiments, the vaccine is administered intradermally, intramuscularly, or intranasally.

In some embodiments, the vaccine contains adjuvant. In some embodiments, the vaccine does not contain adjuvant.

In some embodiments, the vaccine is selected from Fluzone (Trivalent or Quadrivalent; Sanofi Pasteur), Fluarix (Trivalent or Quadrivalent; intradermal; GlaxoSmithKline), FluLaval (Trivalent or Quadrivalent; ID Biomedical Corporation of Quebec; distributed by GlaxoSmithKline), Alfluria (bioCSL), Fluvirin (Novartis Vaccines and Diagnostics), Flucelvax (Novartis Vaccines and Diagnostics), FluMist (MedImmune), and FluBlok (Protein Sciences). In some embodiments, the vaccine is a reformulated version of a vaccine selected from the group consisting of Fluzone (Trivalent or Quadrivalent; Sanofi Pasteur), Fluarix (Trivalent or Quadrivalent; intradermal; GlaxoSmithKline), FluLaval (Trivalent or Quadrivalent; ID Biomedical Corporation of Quebec; distributed by GlaxoSmithKline), Alfluria (bioCSL), Fluvirin (Novartis Vaccines and Diagnostics), Flucelvax (Novartis Vaccines and Diagnostics), FluMist (MedImmune), and FluBlok (Protein Sciences), wherein the reformulated vaccine has a higher dose than the standard dose version.

In some embodiments, the influenza vaccine is marketed as a high-dose influenza vaccine.

In some embodiments, a dose is considered high if the dose provided to the subject for prevention of pneumonia is increased as compared to the dose in a standard-dose influenza vaccine.

In some embodiments, the vaccine is Fluzone High-Dose, which contains 60 micrograms HA per strain per dose (0.5 mL).

In some embodiments, the vaccine is an inactivated or recombinant vaccine.

In some embodiments, the vaccine has an HA content that is higher than 15 micrograms of HA per strain per each 0.5 mL. In some embodiments, the vaccine is higher than about 15, 20, 24, 30, 35, 40, 45, 50, 55, 60, 65, 70, 75, 80, 85, or 90 micrograms of HA per strain for each 0.5 mL.

In some embodiments, the vaccine is similar to Fluzone ID except that its HA content is higher than about 9, 10, 15, 20, 24, 30, 35, 40, 45, 50, 55, 60, 65, 70, 75, 80, 85, or 90 micrograms of HA per strain for each 0.1 mL. In some embodiments, the vaccine is similar to Flublok except that its HA content is higher than about 45, 50, 55, 60, 65, 70, 75, 80, 85, or 90 micrograms of HA per strain for each 0.5 mL. In some embodiments, the vaccine that is administered to a subject for the prevention of influenza is formulated to have a higher HA content than the HA content of a standard dose vaccine. In some embodiments, the vaccine that is administered to a subject for the prevention of influenza is formulated to have a higher NA content than the NA content of a standard dose vaccine.

In some embodiments, the vaccine is a live-attenuated vaccine.

In some embodiments, the vaccine is similar to Flumist except that it contains more than about $10^{6.5}$-$10^{7.5}$ FFU (fluorescent focus units) of live attenuated influenza virus reassortants.

In some embodiments, the subject is elderly. In some embodiments, the subject is older than about 65 years. In some embodiments, the subject is an adult that is older than about 18 years and younger than about 65 years. In some embodiments, the subject is a child that is younger than about 18 years. In some embodiments, the subject is younger than 5 years, 4 years, 3 years, 2 years, 1 year, or 6 months. In some embodiments, the subject is immune-compromised. In some embodiments, the subject is a pregnant woman.

In some embodiments, the subject has asthma, diabetes, heart disease, HIV, AIDS, or cancer. In some embodiments, the subject had asthma, diabetes, heart disease, HIV, AIDS, or cancer.

In some embodiments, the subject is non-human. In some embodiments, the subject is a horse, poultry, pig, dog, or cat.

Headings are provided in this description for organizational purposes and as an aid to the reader only and are not to be construed as limiting the disclosure in any way.

BRIEF DESCRIPTION OF THE DRAWINGS

FIG. 1 shows the trial design of the FIM12 study. FIM12 compared two influenza vaccines, standard-dose inactivated influenza vaccine IIV-SD (Fluzone®) and high-dose inactivated influenza vaccine IIV-HD (Fluzone High-Dose), over two influenza seasons. This randomized-controlled trial (RCT) enrolled patients 65 years of age or older.

DESCRIPTION OF CERTAIN EMBODIMENTS

Influenza Vaccine for Preventing Pneumonia

The invention comprises vaccine compositions useful in preventing influenza and pneumonia, regardless of the cause of pneumonia.

In one embodiment, a method of preventing pneumonia in a subject comprising administering an influenza vaccine to a subject, wherein the dose of the influenza vaccine is higher than a standard dose influenza vaccine, is encompassed. In one embodiment, use of an influenza vaccine for preventing pneumonia in a subject, wherein the dose of the influenza vaccine is higher than a standard dose influenza vaccine, is encompassed. In one embodiment, use of an influenza vaccine for the manufacture of a medicament for preventing pneumonia in a subject, wherein the dose of the influenza vaccine is higher than a standard dose influenza vaccine, is encompassed. In one embodiment, an influenza vaccine for use in preventing pneumonia in a subject, wherein the dose of the influenza vaccine is higher than a standard dose influenza vaccine, is encompassed.

In one embodiment, a method of preventing pneumonia in a subject comprising administering an influenza vaccine to a subject, wherein the influenza vaccine provides the subject with a higher level of antigen than a standard dose influenza vaccine, is encompassed. In one embodiment, use of an influenza vaccine for preventing pneumonia in a subject, wherein the influenza vaccine provides the subject with a higher level of antigen than a standard dose influenza vaccine, is encompassed. In one embodiment, use of an influenza vaccine for the manufacture of a medicament for preventing pneumonia in a subject, wherein the influenza vaccine provides the subject with a higher level of antigen than a standard dose influenza vaccine, is encompassed. In one embodiment, an influenza vaccine for use in preventing pneumonia in a subject, wherein the influenza vaccine provides the subject with a higher level of antigen than a standard dose influenza vaccine, is encompassed.

In other embodiments, methods of preventing pneumonia in a subject comprising administering an influenza vaccine to a subject, wherein the neuraminidase (NA) content of the influenza vaccine is higher than the NA content of a standard dose influenza vaccine is encompassed. In one embodiment, use of an influenza vaccine for preventing pneumonia in a subject, wherein the NA content of the influenza vaccine is higher than the NA content of a standard dose influenza vaccine, is encompassed. In one embodiment, use of an influenza vaccine for the manufacture of a medicament for preventing pneumonia in a subject, wherein the NA content of the influenza vaccine is higher than the NA content of a standard dose influenza vaccine, is encompassed. In one embodiment, an influenza vaccine for use in preventing pneumonia in a subject, wherein the NA content of the influenza vaccine is higher than the NA content of a standard dose influenza vaccine, is encompassed.

In other embodiments, a method of preventing pneumonia in a subject comprising administering an influenza vaccine to a subject, wherein the haemagglutinin (HA) content of the influenza vaccine is higher than the HA content of a standard dose influenza, is encompassed. In one embodiment, use of an influenza vaccine for preventing pneumonia in a subject, wherein the HA content of the influenza vaccine is higher than the HA content of a standard dose influenza vaccine, is encompassed. In one embodiment, use of an influenza vaccine for the manufacture of a medicament for preventing pneumonia in a subject, wherein the HA content of the influenza vaccine is higher than the HA content of a standard dose influenza vaccine, is encompassed. In one embodiment, an influenza vaccine for use in preventing pneumonia in a subject, wherein the HA content of the influenza vaccine is higher than the HA content of a standard dose influenza vaccine, is encompassed.

The description below applies to the methods, uses, and products disclosed herein. Terms such as "administering," e.g., with respect to doses, particular subjects, etc., encompass products and uses of products "to be administered" at the indicated doses and/or to the indicated subjects, etc.

In other embodiments, the influenza vaccine has a higher amount of one or more of the influenza virus proteins (HA, NA, M1, M2, PB1, PB2, PA, NS1, NS2, and/or NP) when compared to standard dose vaccines.

Types of Pneumonia

In one embodiment the pneumonia is caused by a virus, bacteria, or fungi. In the case of viral pneumonia, the virus may be any virus known to cause pneumonia, including an influenza virus, a respiratory syncytial virus (RSV), a metapneumovirus, an adenovirus, a rhinovirus, a coronavirus, a varicella-zoster virus, and a parainfluenza virus.

In the case of bacterial pneumonia, the bacteria may be any bacteria known to cause pneumonia, including *Streptococcus pneumonia, Staphylococcus aureus, Neisseria meningitides, Mycoplasma pneumonia, Haemophilus influenza, Legionella pneumonia, Legionella* spp., *Chlamydia* spp., including *Chlamydia* pneumonia, and *Chlamydia psittaci, Moraxella* spp., including *Moracella catarrhalis, Streptococcus pyogenes,* including *Streptococcus pyogenes* (Group A), *Pseudomonas aeruginosa*, gram-negative enteric bacilli, methicillin-susceptible *S. aureus*, methicillin-resistant *S. aureus, Haemophilus parainfluenzae, Haemophilus parahaeolyticus, Pseudomonas alcaligenes, Citrobacter freundii, Staphylococcu haemolyticus, Clostridium perfringens,* anaerobes, including *Fusobacterium Prevotella* sp., *Gemella morbillorum, Peptostreptococcus prevotii,* and *Veillonella* sp., *nocardia* sp., coagulase-negative *Staphylococci,* and *Acinetobacter baumannii*.

In the case of fungal pneumonia, the fungus may be any fungus known to cause pneumonia, including a fungus responsible for any of histoplasmosis, coccidioidomycosis, blastomycosis, pneumocystis pneumonia, sporotrichosis, cryptococcosis, aspergillosis, candidiasis, or scedoporiosis.

In some embodiments, the cause of the pneumonia is unknown. In other embodiments, the cause of the pneumonia is determined to be viral and bacterial.

In one embodiment the pneumonia is characterized as community-acquired pneumonia (CAP). In other embodiments the pneumonia is a healthcare-associated pneumonia, which is a pneumonia that develops following a stay in a healthcare facility, including a hospital, long-term care facility, or dialysis center.

In some embodiments, the pneumonia to be prevented by the methods, uses, and products of the invention is not preceded by influenza.

Influenza Vaccines

The influenza vaccine composition, as well as the influenza vaccine used in accordance with the invention, may be any influenza vaccine approved by a body that governs the type of vaccines that may be administered to the public. In certain embodiments, a high-dose vaccine contains high levels of one or more influenza protein(s) (HA, NA, M1, M2, PB1, PB2, PA, NS1, NS2, and/or NP).

In one embodiment, the influenza vaccine is a trivalent vaccine. In another embodiment, the influenza is a quadrivalent vaccine.

The trivalent or quadrivalent vaccine may be produced in avian eggs or may be "egg-free" or "recombinant".

The trivalent or quadrivalent vaccine may be inactivated or live attenuated.

The trivalent or quadrivalent vaccine may be administered intradermally, intramuscularly, or intranasally.

The trivalent or quadrivalent vaccine may be adjuvanted or non-adjuvanted.

The trivalent or quadravalent vaccine may be selected from the group consisting of Fluzone® (Trivalent or Quadrivalent; Sanofi Pastuer), Fluarix (Trivalent or Quadrivalent; intradermal; GlaxoSmithKline), FluLaval (Trivalent or Quadrivalent; ID Biomedical Corporation of Quebec; distributed by GlaxoSmithKline), Alfluria (bioCSL), Fluvirin (Novartis Vaccines and Diagnostics), Flucelvax (Novartis Vaccines and Diagnostics), FluMist (MedImmune), and FluBlok (Protein Sciences).

Dosages

In one embodiment, the influenza vaccine composition of the invention, as well as the influenza vaccine for use in accordance with the invention, are high-dose. A dose of an influenza vaccine is considered high if the amount of antigen provided to the subject is increased as compared to the amount of antigen in a standard dose influenza vaccine. The dose may be increased by administering a greater volume of a vaccine formulated in a standard dosage or by specifically formulating a higher dose vaccine.

Dosages are typically based on HA content. For example, the only high-dose influenza vaccine on the market as of the filing date is Fluzone High-Dose, which contains 60 micrograms HA per strain per dose (0.5 mL). All other currently approved influenza vaccines are considered standard dose. Fluzone High-Dose is contemplated for use in accordance with this invention.

For inactivated and recombinant vaccines (all vaccines named above except Flumist) the HA content is typically 15 micrograms of HA per strain for each 0.5 mL. Thus, in one embodiment, the influenza vaccine of this invention has an HA content that is higher than 15 micrograms of HA per strain per each 0.5 mL. In one embodiment, the influenza vaccine of the invention has an HA content that is higher than about 15, 20, 24, 30, 35, 40, 45, 50, 55, 60, 65, 70, 75, 80, 85, or 90 micrograms of HA per strain for each 0.5 mL.

Standard dose Fluzone ID has an HA content of about 9 micrograms per strain per dose (0.1 mL). For Fluzone ID to be used in the present invention, it must have an HA content that is higher than about 9, 10, 15, 20, 24, 30, 35, 40, 45, 50, 55, 60, 65, 70, 75, 80, 85, or 90 micrograms of HA per strain for each 0.1 mL.

Standard dose Flublok has an HA content of about 45 micrograms per strain per dose (0.5 mL). Despite the higher HA content as compared to other vaccines, Flublok is not considered a "high-dose" vaccine by the FDA because of the lack of comparative clinical trial data for it against standard-dose influenza vaccines. In one embodiment, Flublok is considered a high dose vaccine capable of being used in accordance with the invention. In other embodiments, for Flublok to be used in the present invention, it must have an HA content that is higher than about 45, 50, 55, 60, 65, 70, 75, 80, 85, or 90 micrograms of HA per strain for each 0.5 mL.

Thus, the standard dose vaccines described herein and known to those of skill in the art (those today marketed and those marketed in the future) may be used in accordance with the invention to prevent pneumonia as long as they are reformulated to have a higher HA content than the HA content of a standard-dose influenza vaccine.

Flumist is a live-attenuated vaccine that is administered intranasally. Each 0.2 mL dose of Flumist contains about 10E6.5-7.5 FFU (fluorescent focus units) of live attenuated influenza virus reassortants. For Flumist to be used in the present invention, it must have an FFU content that is higher than about 10E6.5-7.5 FFU per live attenuated influenza virus reassortants.

In some embodiments of the present invention, the influenza virus used in preventing pneumonia have an increased neuraminidase (NA) content as compared to a standard-dose influenza vaccine.

The NA content of the high-dose Fluzone® is also increased versus the standard-dose vaccine. An NA activity assay (optical density [O.D] obtained with a microplate reader assay) determined that the mean NA activity in standard dose influenza vaccine was 23,373. In comparison, the mean NA activity in the high-dose influenza vaccine was 179,454, representing approximately 7.7 times the NA activity in the standard dose influenza vaccine (Cate T R et al. Vaccine 2010; 28:2076-2079).

Thus, in one embodiment, the influenza vaccine of this invention has a NA content that is higher than the NA content of a standard dose influenza vaccine. In one embodiment, the influenza vaccine of the invention has a NA content that has an O.D. higher than about 23,000, 23,373, 23,500, 24,000, 25,000, 30,000, 35,000, 40,000, 45,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, 150,000, 155,000, 160,000, 165,000, 170,000, and 175,000.

In some embodiments of the present invention, the influenza vaccine used in preventing pneumonia have an increased HA, NA, M1, M2, PB1, PB2, PA, NS1, NS2, and/or NP content as compared to a standard dose vaccine.

Treatment Groups

Subjects to be treated by the methods, products, and uses of the invention include any subject capable of receiving an influenza vaccine. In one embodiment, the subject is considered elderly. An elderly human subject is older than about 65 years. In other embodiments, the subject is a healthy adult (older than 18 years), a healthy child (younger than 18 years), an immune-compromised adult or child, a pregnant woman, or an adult or child with asthma, diabetes, heart disease, HIV, AIDS, or cancer. The subject may also be a child younger than 5 years, 4 years, 3 years, 2 years, 1 year, and 6 months.

In other embodiments, the subjects to be treated by the methods, products, and uses of the invention are non-human, including horses, poultry, pigs, dogs, and cats.

Combination Therapy

The high-dose influenza vaccine used in accordance with the invention may be administered alone, or co-administered with at least one additional therapeutic or prophylactic agent. In one embodiment, the at least one additional therapeutic or prophylactic agent is a pneumonia vaccine. Thus, methods of preventing pneumonia, or methods of preventing pneumonia and influenza, comprising co-administering a high-dose influenza vaccine and a pneumonia vaccine are encompassed. Uses of a high-dose influenza vaccine and a pneumonia vaccine for preventing pneumonia, or preventing pneumonia and influenza, wherein the influenza vaccine and pneumonia vaccine are co-administered, are also encompassed. A high-dose influenza vaccine and a pneumonia vaccine for use in preventing pneumonia, or preventing pneumonia and influenza, wherein the influenza vaccine and pneumonia vaccine are co-administered, are also encompassed. Uses of a high-dose influenza vaccine and a pneumonia vaccine for the manufacture of a medicament for preventing pneumonia, or preventing pneumonia and influenza, wherein the influenza vaccine and pneumonia vaccine are co-administered, are also encompassed. The co-administration may be concurrent or sequential. The sequential administration may occur on the same day or on different days. As described herein, the high-dose influenza vaccine may contain more than one influenza protein including combinations of HA, NA, M1, M2, PB1, PB2, PA, NS1, NS2, and/or NP, and any one or all of these proteins may be present at a higher level than in a standard-dose vaccine. Thus, in one embodiment the high-dose influenza vaccine used in accordance with the invention has high HA, NA, M1, M2, PB1, PB2, PA, NS1, NS2, and/or NP, and is given in combination with at least one additional therapeutic or prophylactic agent, such as a pneumonia vaccine.

EXAMPLES

Example 1. Efficacy of Vaccination with High-Dose Inactivated Influenza Vaccine Versus Standard Dose in Prevention of Pneumonia in Elderly Patients A high-dose inactivated influenza vaccine (IIV-HD) has been shown to produce more robust antibody responses and improves protection against influenza illness compared to a standard-dose vaccine (IIV-SD) in elderly patients. In this study, IIV-HD was 24.2% more efficacious than IIV-SD in preventing laboratory-confirmed symptomatic influenza in elderly patients. (DiazGranados C A, et al. *N Engl J Med* (2014) 371 (7):635-645). Herein, IIV-HD was compared with IIV-SD in regards to the ability to decrease the risk of pneumonia, a common and dangerous sequelae or complication to influenza, and also a common and very burdensome infectious illness that can be caused by many other microorganisms in addition to influenza.

The FIM12 study was a double-blind, randomized, active-controlled, multicenter trial that enrolled adults≥65 years. Participants were randomized to receive either IIV-HD or IIV-SD and were followed for 6-8 months post-vaccination for the occurrence of influenza, pneumonia, and serious adverse events (SAEs). SAEs were defined as events leading to death or hospitalization (or its prolongation); considered as life-threatening or medically important; or resulting in disability. The trial was conducted during the 2011-2012 (Year 1) and 2012-2013 (Year 2) influenza seasons. The trial compared IIV-HD (containing 60 micrograms of hemagglutinin per vaccine strain, Fluzone® High-Dose) versus IIV-SD (containing 15 micrograms of hemagglutinin per vaccine strain, Fluzone®).

Figure 1:
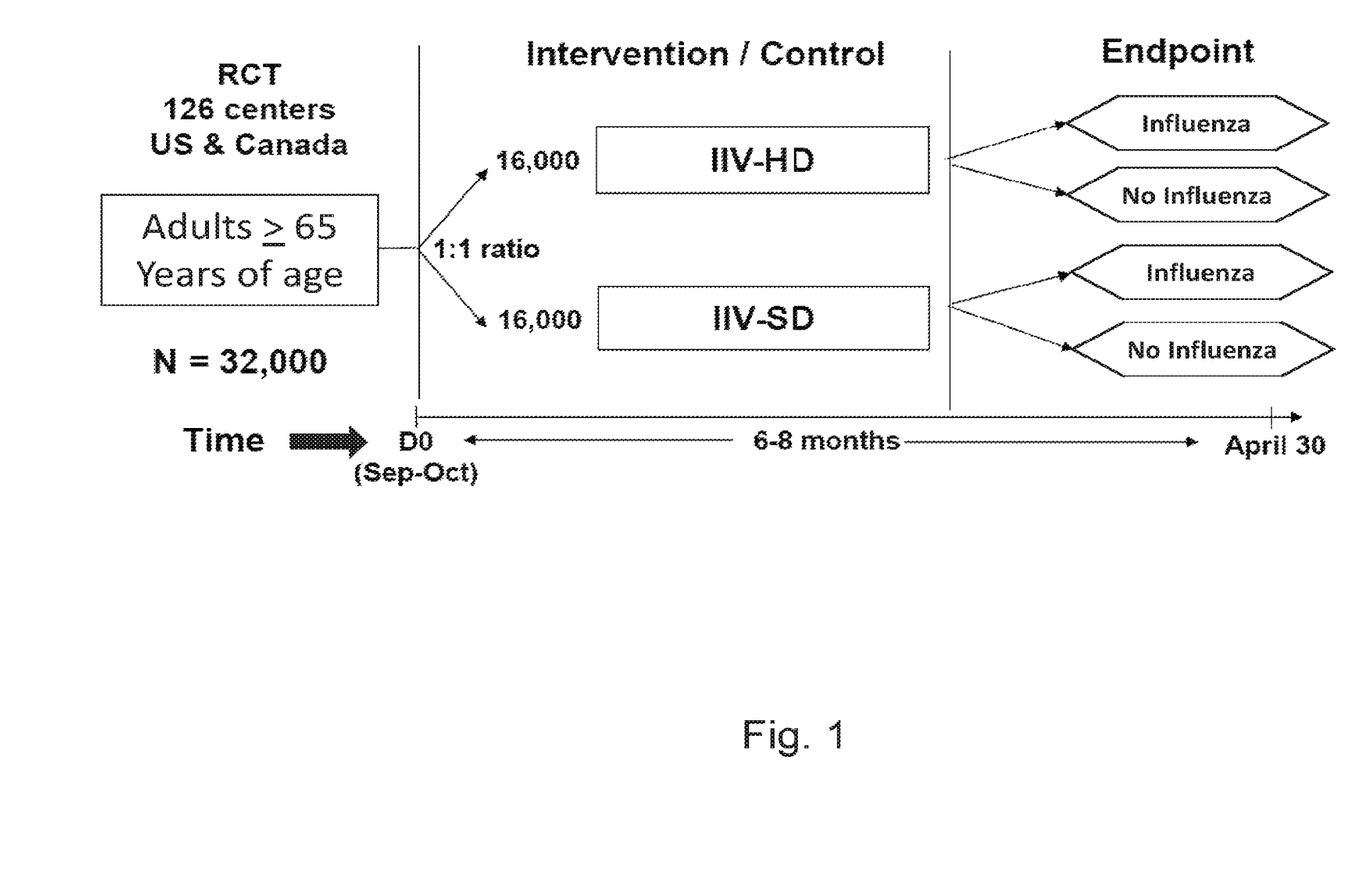

The FIM12 trial (NCT01427309) included 31,989 participants with 15,991 participants randomized to IIV-HD and 15,998 participants randomized to IIV-SD. The design of the FIM12 trial is presented in FIG. 1; note that the actual numbers of patients enrolled in the trial differ slightly from the projected design. Participants were vaccinated in September-October of each season (i.e., Year 1 and Year 2), and participants were followed for 6-8 months post-vaccination (until April 30th, which would be past the normal end of annual influenza season) for the occurrence of influenza, pneumonia, and SAEs.

Results

Figure 2A:
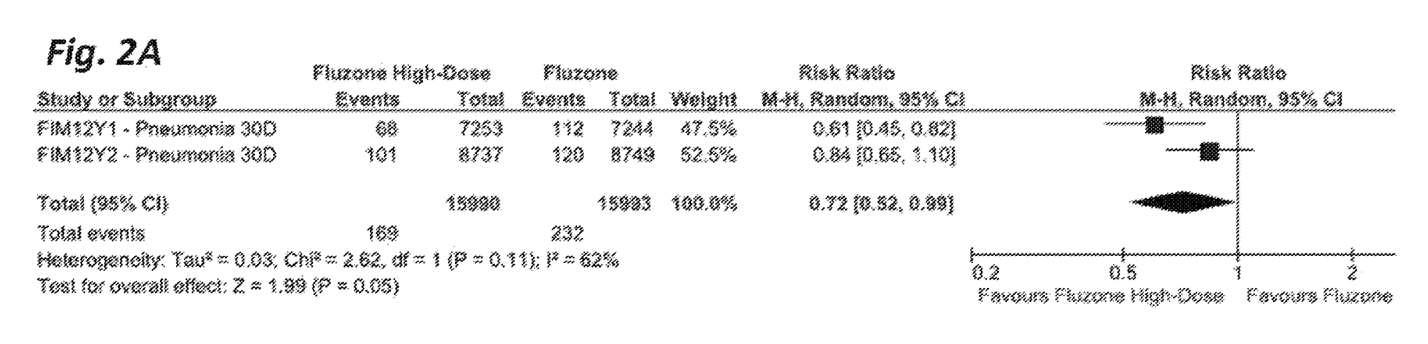
FIGS. 2A and 2B shows the comparison of risk ratio for pneumonia within 30 days of respiratory illness (Pneumonia 30D, FIG. 2A) and serious pneumonia (FIG. 2B) in Trial FIM12 for IIV-SD (labeled as Fluzone®) and IIV-HD (labeled as Fluzone® High-Dose). Analysis was done by year (Y1=year 1; Y2=year 2), and total data for both years are also shown. Heterogeneity is a test of whether the risk ratios are the same in Y1 and Y2; for both pneumonia 30D and serious pneumonia the p-values do not indicate statistically significant differences between the years in this respect, and one therefore concludes there is no strong evidence for a difference in the effect in the two years. CI=confidence interval; M-H=Mantel-Haenszel.
Figure 3:
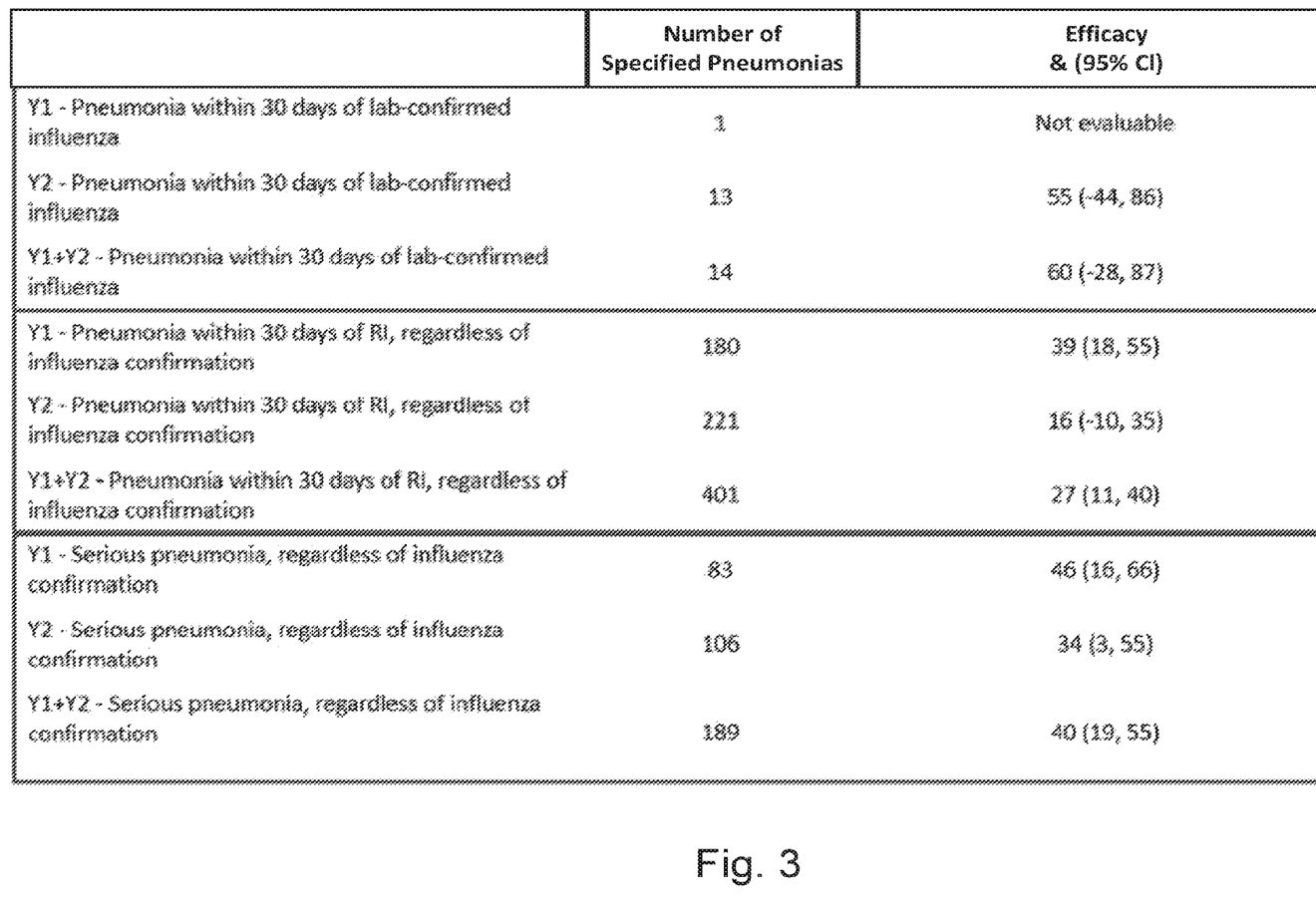
FIG. 3 shows the relative vaccine efficacy of IIV-HD against pneumonia relative to IIV-SD. Pneumonia classification were pneumonia occurring within 30 days of lab-confirmed influenza, pneumonia occurring with 30 days of respiratory illness (RI) regardless of influenza confirmation, and serious pneumonia regardless of influenza confirmation. Efficacy data are presented as (95% confidence interval).

To determine whether IIV-HD protects against pneumonia, the number of pneumonia events occurring within 30 days of a respiratory illness (Pneumonia 30D) for Y1 and Y2 was evaluated, with results shown in FIG. 2A. In combined data from Y1 and Y2, there were 169 events of Pneumonia 30D in the IIV-HD (i.e., Fluzone® High-Dose) and 232 events in the IIV-SD (i.e., Fluzone®). These combined data indicated a relative risk of 0.72 for IIV-HD versus IIV-SD for pneumonia within 30 days of a respiratory illness. As shown in FIG. 3, this corresponds with a 27% relative vaccine efficacy/effectiveness (i.e., 27% reduction in relative risk) in preventing pneumonia within 30 days of a respiratory infection (labeled RI) for IIV-HD versus IIV-SD. Statistical analysis shown in FIG. 2A indicates that this reduction in pneumonia within 30 days of a respiratory infection was statistically significant for IIV-HD versus IIV-SD (P=0.05, test for overall effect). The significance of the finding is further confirmed by the confidence intervals of the vaccine effectiveness estimate (FIG. 3), which indicated a lower bound of the 95% confidence interval of 11%, well above the null value of 0.

Figure 2B:
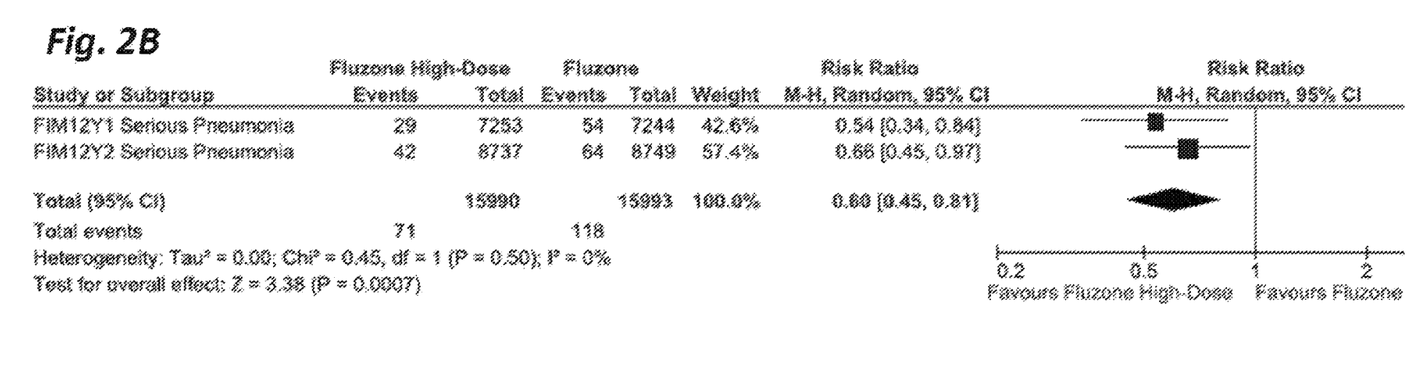

The number of cases of serious pneumonia (irrespective of confirmed influenza infection) was also evaluated. Serious pneumonia was defined as events of pneumonia resulting in death or hospitalization, considered life-threatening or medically important, or resulting in disability. As shown in FIG. 2B, there were a total of 71 events of serious pneumonia in the IIV-HD group compared to 118 events in the IIV-SD group in combined data for Y1 and Y2. These combined data indicated a relative risk of 0.60 for IIV-HD versus IIV-SD for serious pneumonia. As shown in FIG. 3, this corresponded to a relative vaccine efficacy/effectiveness of 40% (i.e., 40% reduction in relative risk) of serious pneumonia for IIV-HD versus IIV-SD. Results shown in FIG. 2B indicate that the efficacy in preventing serious pneumonia was statistically significant for IIV-HD versus IIV-SD (P=0.0007, test for overall effect). The significance of the finding is further confirmed by the confidence intervals of the vaccine effectiveness estimate (FIG. 3), which indicated a lower bound of the 95% confidence interval of 19%, well above the null value of 0.

The relative reduction in pneumonia within 30 days of lab-confirmed influenza was also evaluated. As shown in FIG. 3, there was a 60% relative vaccine efficacy (i.e. reduction in relative risk) of IIV-HD versus IIV-SD for prevention of pneumonia within 30 days of lab-confirmed influenza. However, given the low number of cases, the estimate did not reach statistical significance.

Figure 4:
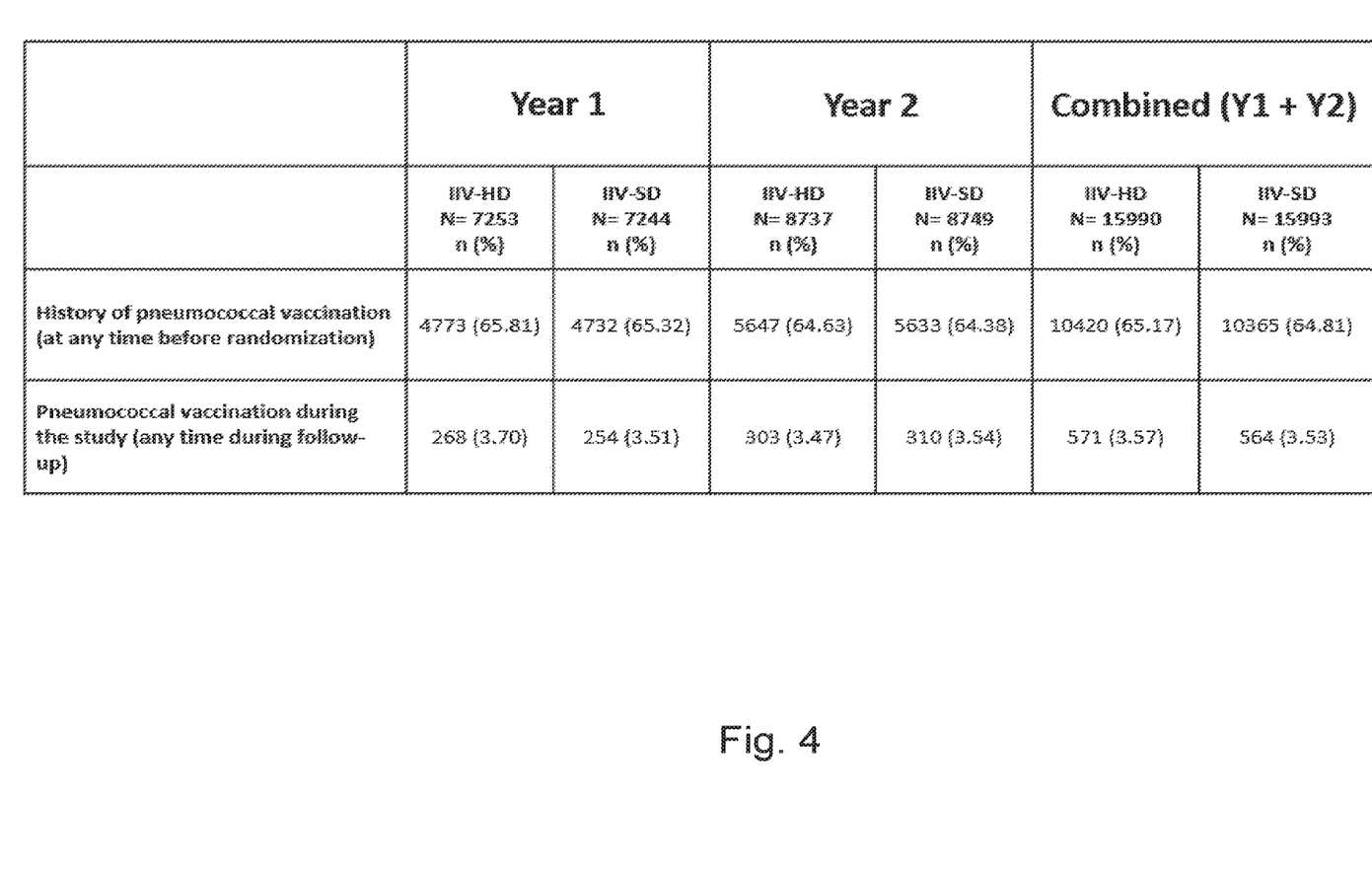
FIG. 4 presents pneumococcus vaccination rates prior to FIM12 randomization and during the trial for IIV-HD and IIV-SD for Y1, Y2, and combined (Y1+Y2).

The potential for pneumococcal vaccination rates to have impacted efficacy measurements of pneumonia prevention for IIV-HD versus IIV-SD was also evaluated, as pneumococcal vaccination is suggested for patients 65 years of age or older and can reduce the risk of pneumonia (see *CDC: Prevention of Pneumonia*). As shown in FIG. 4, vaccination rates for the IIV-HD and IIV-SD groups were essentially the same, indicating that differences in pneumococcal vaccination rates cannot explain the differences in efficacy/effectiveness in preventing pneumonia for IIV-HD versus IIV-SD.

Figure 5:
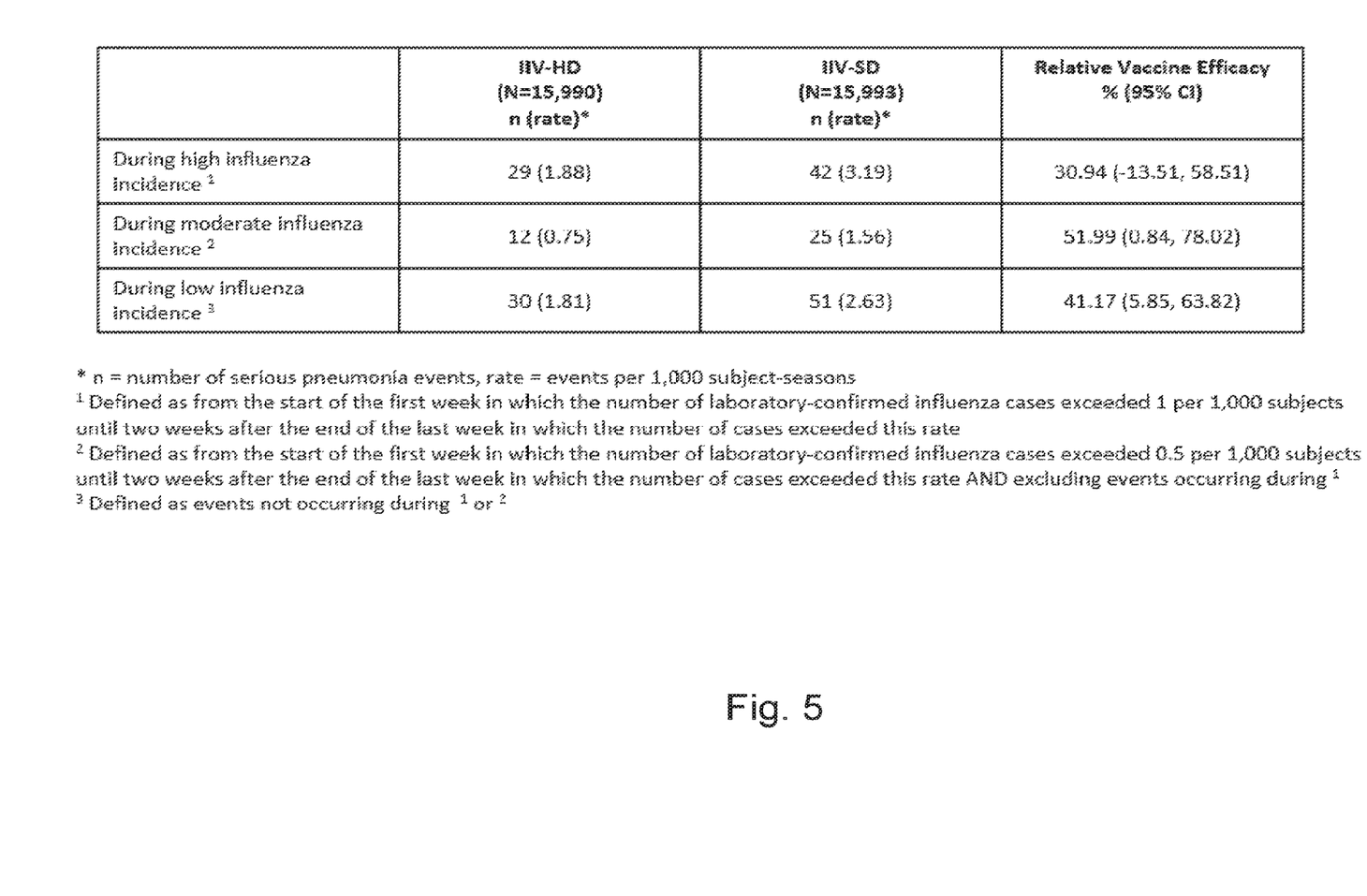
FIG. 5 presents data on the number of serious pneumonia events and the rate of these events following vaccination with IIV-HD or IIV-SD based on the timing of events in relation to the defined level of influenza incidence for the week based on the number of laboratory-confirmed influenza illness observed in the trial. The categories of high, moderate, and low influenza incidence are described in the footnotes.

The relative vaccine efficacy of IIV-HD versus IIV-SD was determined based on differences in the rate of incidence of influenza at the time when the pneumonia event occurred. The actual FIM12 study influenza incidence data was used to determine periods of high, moderate, and low incidence of influenza, as described in FIG. 5. Data confirmed that IIV-HD had greater relative vaccine efficacy compared with IIV-SD for periods of high, moderate, and low incidence. Therefore, the higher relative vaccine efficacy of IIV-HD versus IIV-SD was consistent during all incidence periods.

The data presented in FIGS. 1-5 indicated significant reductions in the incidence of pneumonia, including serious pneumonia, following vaccination with IIV-HD compared with IIV-SD. As data from the same trial indicated that IIV-HD was 24.2% more efficacious than IIV-SD in preventing laboratory-confirmed symptomatic influenza in elderly patients, the data on reduction of risk of pneumonia shown in FIGS. 2 and 3 support an unexpectedly large effect of IIV-HD to reduce pneumonia compared with IIV-SD. The efficacy of IIV-HD significantly reduced the risk of serious pneumonia (relative vaccine efficacy of 40%, see FIG. 3). These data support the use of high-dose influenza vaccine, including IIV-HD, to reduce the risk of pneumonia. These data also support the use of high-dose influenza vaccine, including IIV-HD, to reduce the risk of pneumonia in elderly patients who have increased risk of pneumonia and complications resulting from pneumonia.

The FIM12 study was characterized by intensive surveillance for detection of influenza respiratory illness. The study surveillance included active surveillance, by which a call-center called all study participants twice weekly (during periods of high influenza activity) or weekly (at other times during the influenza season) to inquire about the occurrence of any new or exacerbated respiratory illnesses. If a new or exacerbated illness was reported, the study sites were to collect a nasopharyngeal sample within 5 days of the illness start for influenza testing and detection. We therefore believe that the study had the appropriate design to detect most of the illnesses due to influenza infection occurring in the study participants. This provides an opportunity to evaluate how likely is to attribute the pneumonias reported during the study to influenza (directly as "influenza pneumonias" or indirectly as pneumonias complicating influenza illness). To evaluate this, we ascertained how many of the Pneumonia 30D and serious pneumonias reported in the study occurred within 30 days of laboratory-confirmed influenza. It turns out that only 14 of the 401 reported Pneumonia 30D (3.5%) occurred within 30 days after laboratory-confirmed influenza illness. For the Pneumonias 30D that occurred after a respiratory illness that was not confirmed to be influenza by laboratory methods, the relative vaccine efficacy/effectiveness was 26% and still statistically significant. Similarly and even more importantly, only 4 of the 189 reported Serious Pneumonias (2.1%) occurred within 30 days after laboratory-confirmed influenza illness (with 3 of these confirmations occurring outside of study procedures). For the Serious Pneumonias reported at any time during study surveillance that did not occurred within 30 days of laboratory-confirmed influenza, the relative vaccine efficacy/effectiveness was 38% and highly statistically significant. Therefore, the high-dose influenza vaccine is showing an effect in preventing pneumonia for pneumonias that cannot be classified as related to laboratory-confirmed influenza illness. This indicates that even if the study missed some laboratory-confirmed influenza infections, the high-dose influenza vaccine is very likely having an important preventive effect on pneumonia etiologies other than influenza.

Example 2. Reductions in Hospitalizations and
Serious Adverse Events Following Administration
of IIV-HD Versus IIV-SD Based on results on the reduction in risk of pneumonia, the efficacy of IIV-HD versus IIV-SD was also determined for the potential to reduce all-cause hospitalization and serious cardio-respiratory events for the 6-8 month post-vaccination period of the trial (as described in FIG. 1). SAEs were defined as events that lead to death or hospitalization (or its prolongation); that are considered as life-threatening or medically important; or that result in disability. Based on available medical information, the diagnoses associated with all SAEs were reported.

Figure 6:
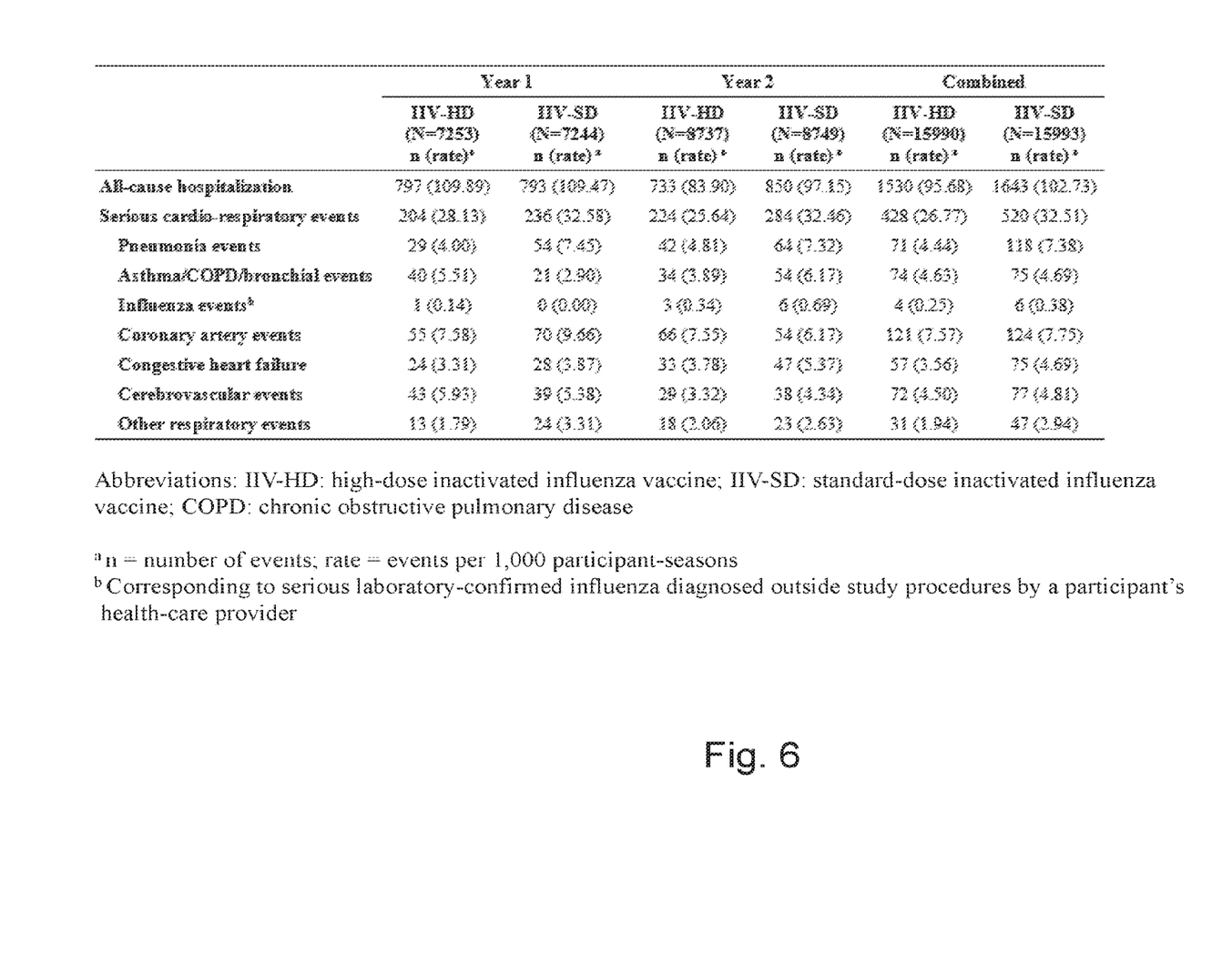
FIG. 6 presents rates of all-cause hospitalization and serious cardio-respiratory events possibly related to influenza within the intent-to-treat population for IIV-HD and IIV-SD for Y1, Y2, and combined (Y1+Y2) combined analysis.
Figure 7:
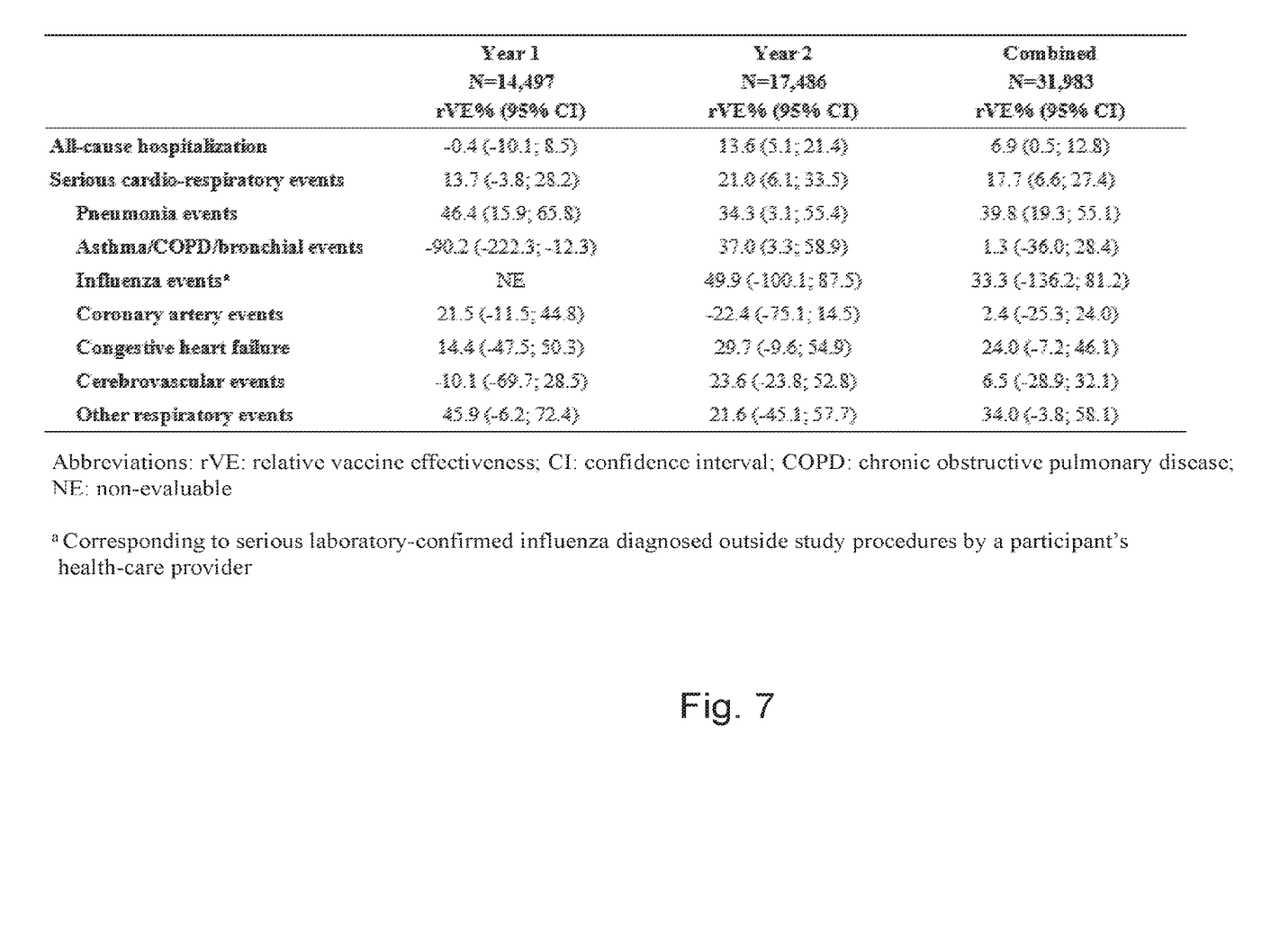
FIG. 7 presents the relative vaccine effectiveness (rVE) of IIV-HD compared with IIV-SD in preventing all-cause hospitalization and serious cardio-respiratory events possibly related to influenza within the intent-to-treat population for Y1, Y2, and combined (Y1+Y2) analysis.
Figure 8:
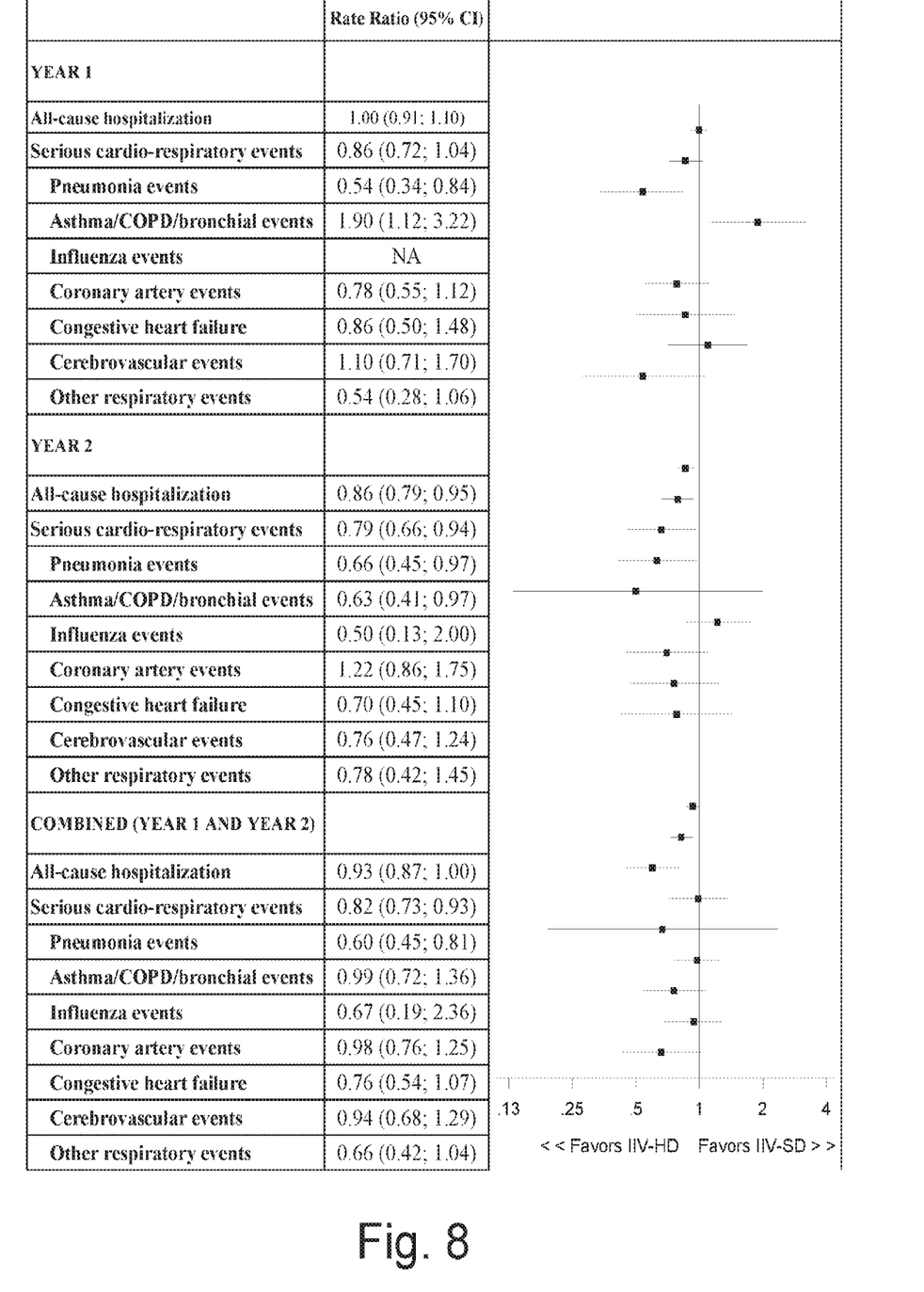
FIG. 8 shows the rate ratios (IIV-HD/IIV-SD) for all-cause hospitalization and serious cardio-respiratory events possibly related to influenza (intent-to-treat analysis). Each horizontal line represents the 95% confidence interval of the rate ratio for each comparison, with the center being the corresponding point estimate. The vertical line represents the null value of 1. Horizontal lines that do not intersect with the vertical line are statistically significant. Point estimates to the left of vertical line favor IIV-HD, and those to the right favor IIV-SD. "Influenza Events" refer to serious laboratory-confirmed influenza diagnosed outside study procedures by a participant's health-care provider.
Figure 9:
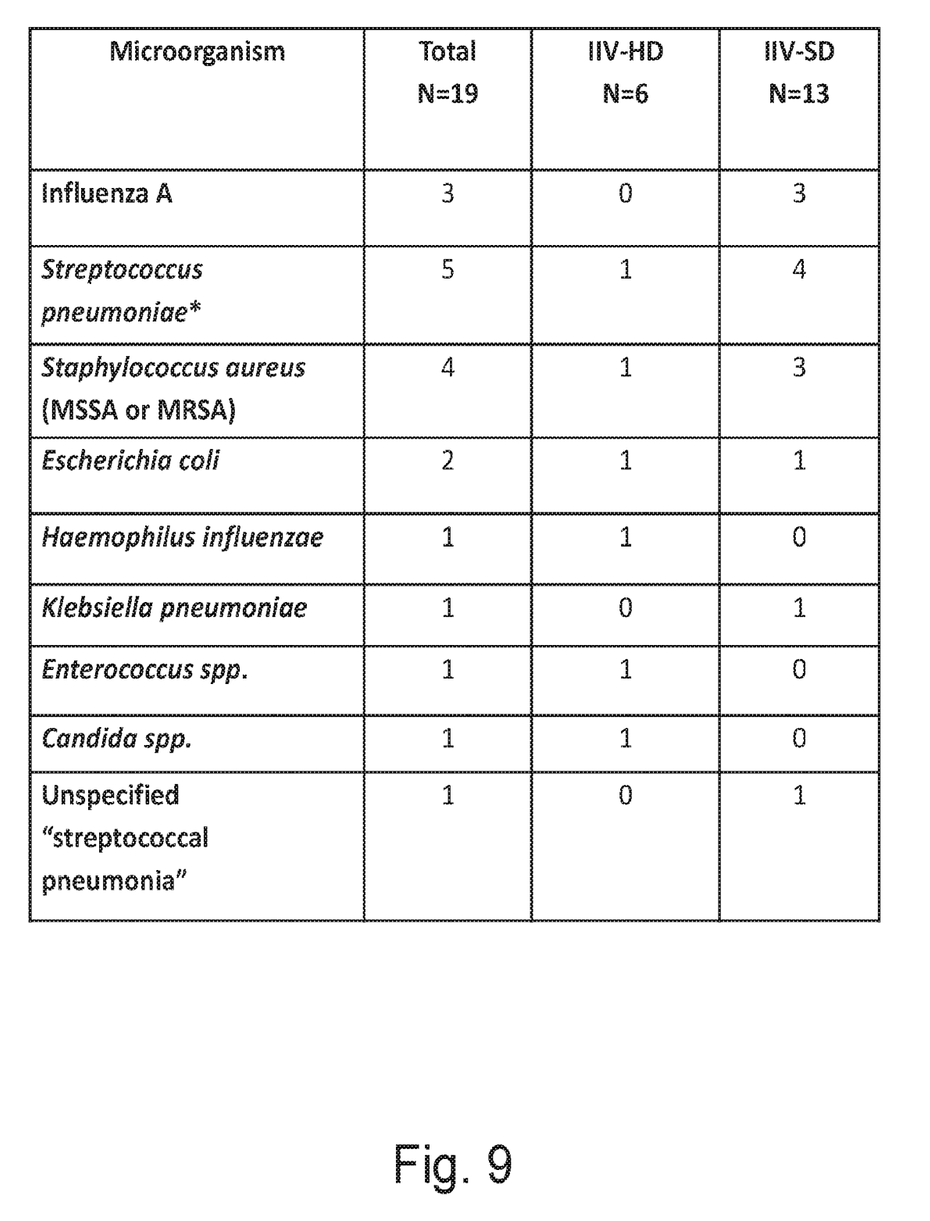
FIG. 9 shows the etiology of the "Serious Pneumonia" narrated in the FIM12 study, based on SAE narratives. Note that for one event, S. pneumonia was isolated from blood cultures, and respiratory cultures revealed E. coli, Pseudomonas, and Group C streptococci (only S. pneumonia counted in the table for this event).

As shown in FIG. 6, there were a total of 3,173 all-cause hospitalization events with a combined rate (events per 1,000 participant-seasons for Y1+Y2) of 95.68 for IIV-HD and 102.73 for IIV-SD. FIG. 7 shows the relative vaccine efficacy of IIV-HD versus IIV-SD for Y1, Y2, and combined data for all-cause hospitalization. Data indicated that while there was very little difference between the rates for Y1, there was a 13.6% relative vaccine efficacy for the all-cause hospitalization rates for IIV-HD versus IIV-SD in Y2. The greater relative vaccine efficacy seen in Y2 may be due to the higher influenza virulence and the greater mismatch between the strains in the vaccine in Y2 versus the predominant circulating strains in that influenza season (as previously discussed in DiazGranados 2014).

Serious adverse events were also assessed in the FIM12 trial. A total of 1,347 SAE preferred terms in the trial for Y1 and Y2 were independently reviewed by two physicians (blinded to the participant's treatment group) using the Medical Dictionary for Regulatory Activities versions 14.0 (for Year 1) and 15.0 (for Year 2) (see Brown E G, et al. (1999) *Drug Saf* 20(2):109-17). A total of 948 serious cardio-respiratory events were adjudicated as possibly related to influenza. Rates of serious cardio-respiratory events for IIV-HD and IIV-SD are shown in FIG. 6; note that the data on serious pneumonia events were also presented in FIG. 3. The rates of influenza in FIG. 6 correspond to serious laboratory-confirmed influenza diagnosed outside study procedures by a participant's health-care provider; therefore, these are different values than those that were used to determine efficacy of the vaccine.

The relative vaccine efficacy (rVE) to reduce serious cardio-respiratory events of IIV-HD compared with IIV-SD is shown in FIG. 7. Rates of serious cardio-respiratory events were lower for IIV-HD than for IIV-SD in both Y1 and Y2 for the events of pneumonia, other selected respiratory events, and heart failure, as evidenced by an rVE greater than 30% for the combined data of Y1 and Y2 for IIV-HD versus IIV-SD. Also the aggregate occurrence of any serious cardio-respiratory event possibly related to influenza was also lower for IIV-HD versus IIV-SD with an rVE of 17.7% for combined data from Y1 and Y2.

The data in FIGS. 6 and 7 support the greater relative efficacy of high-dose influenza vaccine, including IIV-HD, versus IIV-SD for reducing all-cause hospitalization and some serious cardio-pulmonary events in elderly patients. Compared with IIV-SD, IIV-HD produced greater reduction in all-cause hospitalization and pneumonia, other selected respiratory events, and heart failure over two influenza seasons.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/-5-10% of the recited range) that one of ordinary skill in the art would consider equivalent to the recited value (e.g., having the same function or result). In some instances, the term about may include numerical values that are rounded to the nearest significant figure.

What is claimed is:

1. A method for preventing pneumonia in a subject comprising: (a) identifying a subject at risk of serious pneumonia; and (b) administering an influenza vaccine to the subject, wherein the dose of influenza vaccine administered to the subject is higher than a standard-dose influenza vaccine, wherein the vaccine is administered for active immunization against pneumonia in the subject, wherein the pneumonia is caused by a virus, bacterium, or fungus, and wherein the pneumonia is serious pneumonia.

2. A method of preventing pneumonia in a subject comprising: (a) identifying a subject at risk of serious pneumonia; and (b) administering an influenza vaccine to the subject, wherein (i) the content of one or more influenza protein(s) in the influenza vaccine is higher than the content of the influenza protein(s) in a standard-dose influenza vaccine, wherein said influenza protein(s) are selected from HA, NA, M1, M2, PB1, PB2, PA, NS1, NS2, and NP; and/or (ii) the influenza vaccine provides more antigen to the subject as compared to a standard-dose influenza vaccine, wherein the antigen is one or more of HA, NA, M1, M2, PB1, PB2, PA, NS1, NS2, and NP, wherein the pneumonia is caused by a virus, bacterium, or fungus, and wherein the pneumonia is serious pneumonia.

3. The method of claim 1, wherein the pneumonia is caused by a virus selected from influenza virus, respiratory syncytial virus (RSV), metapneumovirus, adenovirus, rhinovirus, coronavirus varicella-zoster virus, and parainfluenza virus; the pneumonia is caused by a bacterium selected from *Streptococcus pneumoniae, Staphylococcus aureus, Neisseria meningitides, Mycoplasma pneumonia, Haemophilus influenae, Legionella pneumonia, Legionella* spp., *Chlamydia* spp., including *Chlamydia* pneumonia and *Chlamydia psittaci, Moraxella* spp., including *Moraxella catarrhalis, Streptococcus pyogenes*, including *Streptococcus pyogenes Pseudomonas aeruginosa*, gram-negative enteric bacilli, methicillin-susceptible *S. aureus*, methicillin-resistant *S. aureus, Haemophilus parainfluenae, Haemophilus parahaemolyticus, Pseudomonas alcaligenes, Citrobacter freundii, Staphylococcus haemolyticus, Clostridium perfringens*, anaerobes, including *Fusobacterium* sp., *Prevotella* sp., *Gemella morbillorum, Peptostreptococcus prevotii, Veillonella* sp., *Nocardia* sp., coagulase-negative *Staphylococci*, and *Acinetobacter baumannii*; the pneumonia is caused by a fungus associated with at least one of histoplasmosis, coccidioidomycosis, blastomycosis, pneumocystis pneumonia, sporotrichosis, cryptococcosis, aspergillosis, candidiasis, or scedoporiosis; the pneumonia is caused by a virus and a bacterium; or the pneumonia is caused by infection with influenza virus.

4. The method of claim 1, wherein the pneumonia is a community-acquired pneumonia (CAP).

5. The method of claim 1, wherein the pneumonia is a healthcare-associated pneumonia.

6. The method of claim 1, wherein the pneumonia is not preceded by influenza.

7. The method of claim 3, wherein the pneumonia is preceded by, or concurrent with influenza.

8. The method of claim 2, wherein the vaccine administered to the subject has a haemagglutinin (HA) content that is higher than the HA content of a standard-dose influenza vaccine, and/or the vaccine administered to the subject has a neuraminidase (NA) content that is higher than the NA content of a standard-dose influenza vaccine.

9. The method of claim 1, wherein the vaccine administered to the subject is a trivalent vaccine or a quadrivalent vaccine.

10. The method of claim 1, wherein the vaccine administered to the subject is produced in avian eggs, is made by recombinant DNA techniques, is inactivated or live attenuated, and/or is administered intradermally, intramuscularly, or intranasally.

11. The method of claim 1, wherein the vaccine administered to the subject contains adjuvant.

12. The method of claim 2, wherein the vaccine administered to the subject is a reformulated version of a vaccine selected from Fluzone (Trivalent or Quadrivalent; Sanofi Pasteur), Fluarix (Trivalent or Quadrivalent; intradermal; GlaxoSmithKline), FluLaval (Trivalent or Quadrivalent; ID Biomedical Corporation of Quebec; distributed by GlaxoSmithKline), Alfluria (bioCSL), Fluvirin (Novartis Vaccines and Diagnostics), Flucelvax (Novartis Vaccines and Diagnostics), FluMist (MedImmune), and FluBlok (Protein Sciences), wherein the reformulated vaccine has a higher dose than the standard dose version.

13. The method of claim 2, wherein the HA content of the vaccine administered to the subject is higher than about 15, 20, 24, 30, 35, 40, 45, 50, 55, 60, 65, 70, 75, 80, 85, or 90 micrograms of HA per strain per dose.

14. The method of claim 2, wherein the vaccine administered to the subject is formulated to have a higher HA content than the HA content of a standard-dose vaccine.

15. The method of claim 2, wherein the vaccine administered to the subject is formulated to have a higher NA content than the NA content of a standard-dose vaccine.

16. The method of claim 1, wherein the subject is about 65 years of age or older or the subject is a child that is about 18 years of age or younger.

17. The method of claim 1, wherein the subject is an adult that is about 18 years of age or older and younger than about 65 years of age.

18. The method of claim 1, wherein the subject is immune-compromised, the subject is a pregnant woman, the subject has or had asthma, diabetes, heart disease, HIV, AIDS, or cancer, and/or the subject is younger than 5 years, 4 years, 3 years, 2 years, 1 year, or 6 months.

19. The method of claim 1 wherein the pneumonia is caused by a non-influenza pathogen.

20. A method for preventing pneumonia caused by a non-influenza pathogen in a subject comprising: (a) identifying a subject at risk of pneumonia; and (b) administering an influenza vaccine to the subject, wherein the dose of influenza vaccine administered to the subject is higher than a standard-dose influenza vaccine, wherein the vaccine is administered for active immunization against pneumonia in the subject, and wherein the pneumonia is caused by a non-influenza virus, bacterium, or fungus.

21. The method of claim 20, wherein the pneumonia is not preceded by or concurrent with influenza.

* * * * *

UNITED STATES PATENT AND TRADEMARK OFFICE
CERTIFICATE OF CORRECTION

| | |
|---|---|
| PATENT NO. | : 11,305,005 B2 |
| APPLICATION NO. | : 15/738417 |
| DATED | : April 19, 2022 |
| INVENTOR(S) | : DiazGranados et al. |

It is certified that error appears in the above-identified patent and that said Letters Patent is hereby corrected as shown below:

In the Claims

Column 14 In Claim 3, Line 49, "*influenae*," should read --*influenzae*,--.

Column 14 In Claim 3, Line 50, "*Chlamydia* pneumonia" should read --*Chlamydia pneumonia*--.

Column 14 In Claim 3, Line 53, "*pyogenes Pseudomonas aeruginosa*," should read --*pyogenes* Group A, *Pseudomonas aeruginosa*,--.

Column 14 In Claim 3, Line 55, "*parainfluenae*," should read --*parainfluenzae*,--.

Column 15 In Claim 12, Line 35, "standard dose" should read --standard-dose--.

Signed and Sealed this
Fourteenth Day of June, 2022

Katherine Kelly Vidal
*Director of the United States Patent and Trademark Office*